United States Patent [19]

Chamberlain

[11] Patent Number: 5,525,575
[45] Date of Patent: Jun. 11, 1996

[54] SPRAYABLE AGRICULTURAL COMPOSITIONS

[75] Inventor: Peter Chamberlain, Shipley, England

[73] Assignee: Allied Colloids Limited, Bradford, England

[21] Appl. No.: 65,047

[22] Filed: May 24, 1993

Related U.S. Application Data

[63] Continuation of Ser. No. 857,258, Mar. 25, 1992.

[30] Foreign Application Priority Data

Mar. 26, 1991 [GB] United Kingdom .................. 9106409

[51] Int. Cl.$^6$ ...................................... A01N 25/30
[52] U.S. Cl. ............... 504/116; 504/206; 504/212; 504/235; 504/244; 504/251; 504/255; 504/270; 504/323; 504/345; 71/DIG. 1
[58] Field of Search ...................... 504/116, 206, 504/244, 251, 323, 345; 71/DIG. 1

[56] References Cited

U.S. PATENT DOCUMENTS

| | | | |
|---|---|---|---|
| 3,360,356 | 12/1967 | Vartiak | 71/65 |
| 3,813,345 | 5/1974 | Urton | 252/312 |
| 4,126,443 | 11/1978 | Gadea | 71/92 |
| 4,267,280 | 5/1981 | McCormick | 71/DIG. 1 |
| 4,657,581 | 4/1987 | Takematsu et al. | 71/118 |
| 5,037,654 | 8/1991 | Puritch et al. | 424/405 |
| 5,118,338 | 6/1992 | Moller | 71/DIG. 1 |
| 5,147,444 | 9/1992 | Decor et al. | 71/86 |

FOREIGN PATENT DOCUMENTS

| | | |
|---|---|---|
| 785706 | 5/1968 | Canada . |
| 1023264 | 12/1977 | Canada . |
| 0055857 | 7/1982 | European Pat. Off. . |
| 0245970 | 11/1987 | European Pat. Off. . |
| 0365279 | 4/1990 | European Pat. Off. . |
| 0376910 | 7/1990 | European Pat. Off. . |
| 1285930 | 1/1962 | France . |
| 58-72501 | 4/1983 | Japan . |
| 61-78701 | 4/1986 | Japan . |
| 831344 | 3/1960 | United Kingdom . |
| 1506568 | 4/1978 | United Kingdom . |
| 2107986 | 5/1983 | United Kingdom . |
| WO88/10069 | 12/1988 | WIPO . |
| WO89/03175 | 4/1989 | WIPO . |

OTHER PUBLICATIONS

European Search Report, European Patent Appl. No. EP 92 30 2455, dated Jun. 26, 1992.

Sundaram, A., J. Environ, Sci. Health, B25(3), 309–332 (1990).

*Primary Examiner*—S. Mark Clardy
*Attorney, Agent, or Firm*—Dickstein, Shapiro & Morin

[57] ABSTRACT

The systemic activity of systemic active ingredients in sprayed foliar systemic compositions is improved by incorporating water soluble polymer. The polymer can have a molecular weight sufficiently low that its presence does not substantially affect the spray pattern of the composition and such that the polymer can initially be supplied as an aqueous solution having 1 to 25% concentration. When the active ingredient is water soluble, for instance glyphosate or chlormequat, a concentrate can comprise an aqueous solution of the active ingredient and the polymer.

12 Claims, No Drawings

SPRAYABLE AGRICULTURAL COMPOSITIONS

This application is a continuation of application Ser. No. 07/857,258, filed Mar. 25, 1992.

This invention relates to foliar systemic compositions, that is to say compositions that are to be sprayed on to plants to administer an agriculturally useful active ingredient that is absorbed through the leaves and into the plant so as subsequently to achieve systemically an agriculturally useful effect such as a herbicidal, fungicidal, insecticidal or plant growth regulatory effect. In particular, the invention relates to sprayable compositions and to concentrates from which they can be obtained.

Agriculturally active ingredients are often provided to the user as a concentrate, which the user can then dilute to form an aqueous sprayable composition. Many forms of agricultural concentrates are known and these consist of the active ingredient and a carrier, that can include various components. It is known to include polymeric material as part of the carrier in some agricultural concentrates.

When the concentrate is a solution in water or organic solvent, it is very rare to include polymeric material. However when the concentrate is a dispersion in water it is common to include a small amount of polymeric thickener and when the concentrate is a dispersible grain it is common to include a small amount of polymeric binder. A wide variety of polymers have been mentioned in the literature as thickeners and binders (for instance the cellulosic, acrylamide, vinyl alcohol and other polymers proposed in U.S. Pat. No. 4,657,781) but in practice very few polymers have been used. For instance the thickener is almost always xanthan gum. The thickeners and binders used in agricultural concentrates generally have high molecular weight, in order that they can impart the desired thickening or binding effect. They are generally present in a minor amount relative to the active ingredient, for instance less than 0.1 parts polymer per part by weight active ingredient.

In U.S. Pat. No. 4,126,443 a very small amount of low molecular weight hydrolysed acrylamide is incorporated into an aqueous concentrate of a particular herbicide in order to prevent crystallisation within the concentrate. The polymer is formed of 50 to 99% acrylic acid groups 1 to 50% acrylamide groups and is present in the concentrate in an amount that is recommended to be below 640ppm (0.064%) although in one example the amount is 0.5%. The amount of active ingredient in the concentrate is from 20 to 40% and so when this is diluted to form a sprayable composition the concentration of polymer in the sprayable composition will be only a few parts per million.

It is also known to include polymers in the agricultural composition that is to be applied, so as to modify the properties of that composition. For instance in EP-A-55857 a particular carbamate insecticide is blended with an excess of various film-forming polymers and applied as a film from an ethanol solution, and it is suggested that the effect of the polymer is to alter the crystallisation properties of the carbamate when the solvent evaporates and a film is formed. There is no suggestion the solution should be sprayed and the carbamate is not a foliar systemic active ingredient. Indeed the teaching in this patent (to adjust the crystallisation properties) is clearly unrelated to systemic activity which requires absorption of the active ingredient, presumably while still in the liquid phase, through the leaves into the plant. The preferred polymers in EP 55857 are said to be water soluble cellulose derivatives but polyacrylamides, ethylene oxide resins and water insoluble polyamides, esters and other polymers are mentioned including very high molecular weight polyethylene oxide. Since the compositions are cast as a film, it is clear that the polymer will have a major effect on the properties of the film and on the properties of the solution before drying.

It is also known to include high molecular weight polymers in agricultural compositions that are to be sprayed so as to have a beneficial effect on the spray pattern of the composition. These materials are generally added to increase the size of the spray droplets so as to reduce drift, and have the consequence of altering and generally reducing the spray angle. Also, such a polymer in the solution may tend to act as a sticker, to promote adhesion of the active ingredient to the leaves so as to improve persistence even if it rains soon after spraying. In practice, the materials that have generally been proposed are reverse phase emulsions, and a typical disclosure is in Canadian patent 1,023,264. Such materials have been commercially available under the name Nalcotrol from Nalco Chemical Company and Bandrift from Allied Colloids Limited.

Despite the proposals in the literature, and the commercial availability of suitable materials, in fact there has been very little use of products such as Nalcotrol and Bandrift. The reason for this is that it seems user did not judge that there was sufficient economic or environmental justification for their use. Also, the larger drop size that is a necessary consequence of reducing spray drift might be expected to reduce coverage and therefore activity.

Also, it appears that there has been some concern that the polymer might interfere with the systemic activity of the active ingredient. Thus in J Environ Sci Health, volume B25(3), 1990, pages 309 to 332 (published after the priority date of this application) Sundaram reported investigations into the effect of Nalcotrol on bioavailability of glyphosate in laboratory trials on seedlings of Trembling Aspen (*Populus tremuloids*). He conducted studies into small differences in the sub-lethal effects of such compositions and concluded that there were no significant differences in the absorption and translocation patterns and growth parameters between plants treated with glyphosate alone and plants treated with glyphosate combined with Nalcotrol.

In PCT WO91/14365 (not published at the priority date hereof) we describe that there is an overall improvement in systemic activity when spray droplets that contact the leaves contain a solution of certain polymers in addition to a solution or emulsion of the systemic active ingredient. In particular, we describe that these benefits can be obtained by incorporating into the solution that is to be sprayed certain reverse phase polymeric compositions. We state that the preferred polymers are polymers of acrylamide and preferred polymers have a viscosity such that they affect the spray drift and spray droplet properties, generally having intrinsic viscosity above 3 dl/g, for instance 7 to 15 dl/g. Thus the reverse phase dispersions that are used may be typical of the spray drift additives such as Bandrift.

It would be desirable to improve the systemic effectiveness of systemic active ingredients in sprayable compositions without affecting the spray pattern of the composition, since this allows the composition to be used under spraying conditions that are not restricted by the presence of the polymer.

When the active ingredient is water soluble, it would also be desirable to provide a fluid, and easily dilutable, concentrate containing both the active ingredient and the polymer dissolved in water.

In one aspect of the invention, a sprayable foliar composition comprises a solution or dispersion of a systemic active ingredient in a continuous aqueous phase and is characterised in that the continuous phase is an aqueous solution of 0.005% to 0.5% (by weight of solution) of a water soluble polymer having a low molecular weight. Preferably this is such that its presence in the composition does not substantially affect the spray pattern of the composition and/or is such that the polymer can conveniently be supplied as an aqueous solution of 1 to 25% polymer.

Another aspect of the invention comprises a method in which such a composition is sprayed on to growing plants and the active ingredient is thereby absorbed from the solution through the leaves of the plants to exert a systemic activity.

Another aspect of the invention comprises an aqueous concentrate that can be diluted in water to form a sprayable foliar systemic composition and that is a solution of water soluble foliar systemic active ingredient and 1 to 25%, by weight of the concentrate, of a water soluble polymer dissolved in the concentrate.

The present invention is based on the surprising discovery that, when one studies a range of plants, there is an overall improvement in systemic activity when the spray droplets that contact the leaves contain a solution of certain polymers in addition to a solution or emulsion of the systemic active ingredient. Thus we have discovered that there is a significant performance benefit in the incorporation of polymers that do not substantially alter the spray pattern of the composition. Thus in the invention the molecular weight and amount of the polymer is generally such that the spray pattern of the composition is substantially unchanged (compared to the corresponding sprayable composition in the absence of polymer) but significant improvement in systemic performance is obtained.

In particular, by incorporating the polymer solution into the sprayed droplets on the leaves it is possible with many substrates to obtain the same systemic activity in the presence of the polymer as is obtained at a much higher concentration of active ingredient in the absence of the polymer. For instance it may be possible on some substrates to halve the concentration of systemic herbicide and yet still obtain a systemic lethal effect on the substrate.

It seems that the presence of the dissolved polymer results in accelerated transport and translocation of the active ingredient into the plants, with consequential improvement in the prospects of lethal effects on the plant. For instance there can be significant translocation within 45 minutes of spraying. It seems that the rain persistence or sticking properties of the sprayed composition is irrelevant to this effect, since the advantage is shown both when rain occurs and when it does not.

Although we do not wish to be bound by theory, it seems that there is some interaction between the cell wall and the sprayed solution of polymer and active ingredient whereby the polymer promotes the transfer of the active ingredient through the cell wall into the cell, but apparently does not promote the reverse transfer of the active ingredient out of the cell. The use of a polymer having pendant amide groups is particularly desirable because of the compatibility between the amide groups and the cell walls, and preferably therefore the polymer is an acrylamide polymer. The use of materials such as ammonium sulphate and urea to improve transport of glyphosate into cell walls is known but the inclusion of such materials tends to result in mere scorch of the leaves, and this is undesirable. By the inclusion of useful amounts of suitable polymer it is possible to achieve improved transport and/or translocation without incurring scorch or other phytotoxic effects.

The use of substantially non-ionic polyacrylamide is particularly preferred because it is effective, toxicologically acceptable, and compatible with a wide variety of active ingredients and other components (such as surfactants) that may be included in the compositions, irrespective of whether these other components are ionic or non-ionic. Also, substantially non-ionic polyacrylamide has less tendency to increase the viscosity of the composition (and thus potentially affect the spray pattern) than would an ionic polymer of the same molecular weight at the same dosage. The preferred polymers are therefore formed of 97 to 100% acrylamide and 3 to 0% sodium acrylate (by weight).

However other suitable polymers can contain up to 20%, or sometimes even up to 49%, by weight of monomers other than acrylamide, with the balance being acrylamide. These other monomers can be non-ionic but are generally anionic or cationic and are usually ethylenically unsaturated.

Thus suitable polymers have a content of sodium acrylate or other anionic groups of for instance up to 10% or even 20%. Another class of suitable polymers are acrylamide cationic polymers, for instance formed from 60 to 99%, often 70 to 90%, by weight acrylamide with the balance being cationic monomer, such as any of the cationic monomers listed below.

The preferred co-monomers are acrylic or allylic monomers that will copolymerise with acrylamide. Suitable cationic monomers include dialkylaminoalkyl -(meth) acrylates and -(meth) acrylamides usually as quaternary or acid addition salts. Suitable anionic monomers include ethylenically unsaturated sulphonic monomers such as 2-acrylamido methyl propane sulphonate and, preferably, carboxylic monomers such as (meth) acrylic acid (usually as water soluble salts).

Instead of using acrylamide polymers, other water soluble polymers, for instance formed from blends of ethylenically unsaturated non-ionic and cationic or anionic monomer can be used provided they give the desired effect. It should however be noted that some polymers will give a negative effect. For instance partially neutralised polyacrylic acid can reduce herbicidal effectiveness.

The molecular weight of the polymer is preferably quite low since this facilitates manufacture, formulation and use, and there is no advantage in the invention in increasing the molecular weight. Generally the preferred molecular weight is such that the polymer has intrinsic viscosity below 4 dl/g and generally below 3 dl/g, but preferably above 0.2 or 0.5 and most preferably above 1 dl/g, with an intrinsic viscosity of around 2 dl/g generally being preferred. Intrinsic viscosity is measured by suspended level viscometer at 25° C. in 1N buffered sodium chloride solution. Molecular weight (determined by gel permeation chromotography) is generally below 4 million and is frequently in the range 100,000 to 1 million, but it can be below 100,000 and as low as, for instance, 30,000 or even less, for instance down to 15,000, 10,000 or even 5,000. However it is considered unacceptable to expose monomeric acrylamide to the environment and the risk of monomeric acrylamide contamination may increase as the molecular weight decreases and this makes it desirable to avoid extremely low molecular weights.

The amount of polymer that is required in the spray solution to achieve improved systemic activity can be determined by routine experimentation and will depend upon the plant, the polymer and the active ingredient. It is generally in the range 0,005 to 0.5% (by weight of solution). In many instances it is desirable to include at least 0.01, and often at least 0.02% in order to obtain a useful effect, and frequently it is found that there is a significant improvement as the concentration increases up to, for instance, about 0.05% or 0.1%. However there is generally no benefit in increasing the polymer concentration above around 0.1 or, at the most, 0.2% but if desired higher amounts can be used.

Whether or not the presence of the chosen amount of the chosen polymer does substantially alter the spray pattern of the composition can easily be determined merely by spraying the composition, with and without the dissolved polymer in it, through a spray bar that is otherwise unchanged for both tests. Another way of determining whether the spray pattern is substantially altered is by observing the particle size of the spray droplets. Conventional spray-drift polymers and stickers will tend to result in a significant increase in average particle size of the spray droplets. By saying that the presence of the polymer does not substantially affect the spray pattern of the composition we mean that the spray pattern (or the particle size) is affected much less by the presence of the defined polymer than when conventional amounts (typically 0.02%) of a conventional spray drift polymer or sticker is added, and preferably the droplet size and the spray pattern of the composition of the invention is substantially the same as the droplet size and the spray pattern of the same composition from which the polymer has been omitted.

Although it is preferred that the polymer does not substantially affect the spray pattern of the composition, the invention can also include compositions in which the polymer can have some effect on the spray pattern. Such compositions are distinguished from, for instance, the compositions in WO91/14365 preferably by forming the compositions by diluting an aqueous solution of from 1 to 25% by weight of the polymer, either as a polymeric additive to the composition or as a concentrate containing the active ingredient and the polymer.

Thus whereas the polymers traditionally used as spray drift inhibitors cannot conveniently be supplied to the user as a solution, because of the high viscosity of aqueous solutions of them, in the invention the polymer can have such a low molecular weight that it can be supplied to the user as a fluid solution of polymer in water. The polymer solution that is supplied to the user preferably has a polymer content of at least 3% and often at least 5% (these concentrations being inpracticable for spray drift inhibitors). Although the amount is often below at least 10%, it can be more. Generally it is unnecessary for the amount of polymer to be too high, for instance above 25%, and generally it is convenient for the polymer concentration to be below 20% and more usually below 15%.

When the active ingredient is water soluble, it is generally supplied as an aqueous concentrate, i.e., a solution of the active ingredient in water. The amount of active ingredient will be selected according to its solubility, but is often above 10% and frequently above 30%, and can be as high as 60% or even 75% by weight.

Preferred water soluble active ingredients are Glyphosate, Chlormequat, Diquat, Clopyralid and hormone weedkillers, such as Mecoprop, 2,4-D, CMPP or MCPA, for instance supplied as a potassium, sodium or amine or other water soluble salt.

It is particularly preferred to provide an aqueous concentrate that is a solution of Chlormequat or other water soluble active ingredient and low molecular weight polyacrylamide or other polymer. The amount of active ingredient can be conventional for that active ingredient. The amount of polymer is generally at least 1%, often at least 3% and frequently at least 5%. Usually it is not more than 10% but it can be more, for instance up to 15, 20 or even 25% by weight.

The amount of polymer can, of course, be less than 1% if the concentrate is more dilute than conventional agricultural concentrates.

Instead of supplying the active ingredient as an aqueous solution, it can be supplied in any of the other conventional forms such as oil-in-water emulsions, suspension concentrates, emulsifiable concentrates, and water dispersible grains.

Water insoluble active ingredients that can be used include Bromoxynil, Ioxynil and Pentanochlor. Others, and the form in which they are conveniently supplied, include Fenoxaprop-ethyl (oil-in-water emulsion), Quizalofop-ethyl (suspension concentrate), Fluroxypyr (emulsifiable concentrate), Metsulfuron-methyl (water-dispersible grain), and Isoproturon (suspension concentrate).

The improved systemic effectiveness of the active ingredients that is achieved by the invention has never previously been reported and the invention includes such uses where the active ingredient is glyphosate, and in particular such uses when applied to a variety of plant substrates. It is not clear why Sundaram failed to observe the effect, but it is probably a combination of factors, namely he was determining the sub-lethal effect of the composition whereas the invention aims at a lethal effect (when using a herbicide), and his dosages and particular techniques were therefore inadequate to give lethal effects, and he conducted tests on a single plant species.

The amount of active ingredient in the sprayable composition and that is sprayed on to the fields will be selected according to normal recommended instructions except that, as a result of introducing the polymer, the amount can generally be in the range 50 to 80% of the amount that would normally be recommended as optimum.

The invention is of particular value in the herbicidal treatment of a variety of crop areas and these can include forestry; clean-up of cereal crops before harvest; autumn field clean-up; and use on waxy-headed varieties common in Mediteranean climates. In such methods the active ingredient is a herbicide and the method involves killing of the plants. Preferably the area that is sprayed contains a plurality of varieties of plants, most or all of which preferably are killed by the treatment. In other instances there is one persistent weed in an otherwise empty crop area (e.g., couch grass) or there are a plurality of weeds amongst resistant plants such as relatively mature trees.

Although the invention is of particular value with glyphosate and other water soluble materials such as Mecoprop-P and Clopyralid, it is also of value with insoluble materials such as Quizalofop-ethyl, Fluroxypyr, Sethoxydim, Fluazifop-p-Butyl, Fenoxaprop-Ethyl and Metsulfuron-Methyl.

Another important aspect of the invention is the use of Chlormequat as plant growth regulator, e.g., for cereals, in combination with the polymer.

An important result of the invention is that the presence of the polymer results in the active ingredient generally having a better spectrum of activity on a range of plants or pests but it does not guarantee that it will have better activity on every individual plant variety or pest. Accordingly, although there may be an overall improvement in the spectrum of activity against various plants, there may be a few isolated instances where activity is worse with the polymer than without. However this does not detract from the fact that the presence of polymer clearly gives a benefit in the overall spectrum of activity, against other plants, with the result that the invention gives the opportunity for frequently reducing the dosage of active ingredient that is required in general field use.

EXAMPLE 1

Non-ionic polyacrylamide having intrinsic viscosity 2 dl/g is supplied as a 12.5% solution in water. A sprayable composition containing glyphosate is prepared in conventional manner and is either used as such (at 250 or 375 grams active ingredient per hectare) or is used after adding the polymer solution to the glyphosate solution at a dosage of 0.025% polymer.

The resultant solutions were sprayed on to winter barley (variety Igri) at the 2 leaf growth stage in trays of compost in a growing room. The leaves of the sprayed plant were subsequently cut down just above the growing point to remove any non-translocated glyphosate and after 16 days an assessment was made as to the number of plants that had died or were dying. When the glyphosate was sprayed at 250 grams the estimate of kill was 20% without polymer and 50% with polymer. When the glyphosate was sprayed at the rate of 375 grams, the estimate of kill was 40% without the polymer and 85% with the polymer.

EXAMPLE 2

The process of Example 1 was repeated at different dosages of glyphosate isopropylamine salt per hectare in 250 liters water with and without 0.1% of the polyacrylamide in the spray solution. Five days after application, the plants were cut off just above the growing point and six days later the regrowth was cut and weighed and an assessment made of the number of dead plants. The results are in Table 1.

TABLE 1

| Glyphosate (g/ha) | 0 | 120 | | 240 | | 360 | |
|---|---|---|---|---|---|---|---|
| Polymer (%) | 0 | 0 | 0.1 | 0 | 0.1 | 0 | 0.1 |
| Regrowth (%) | 100 | 100 | 81.6 | 86.8 | 27.8 | 8.1 | 3.4 |
| Kill (%) | 0 | 0 | 18.4 | 13.2 | 72.2 | 91.9 | 96.6 |

EXAMPLE 3

The process of Examples 2 was repeated in a different series of trials except that different amounts of the polymer were used and the assessment was made after 15 days. The results are shown in Table 2.

TABLE 2

| Glyphosate (g/ha) | 0 (Control) | 375 | 375 | 375 | 375 |
|---|---|---|---|---|---|
| Polymer (%) | 0 | 0 | 0.025 | 0.05 | 0.1 |
| Regrowth (%) | 100 | 62.1 | 56.7 | 43.0 | 30.2 |
| Kill (%) | 0 | 40 | 40 | 50 | 70 |

EXAMPLE 4

The process of Example 2 was repeated with non-ionic polyacrylamide as in Example 2, with anionic polyacrylamide IV 2.7 dl/g formed from 72% acrylamide and 28% sodium acrylate, and with cationic polyacrylamide having IV 3 dl/g and formed from 90% acrylamide and 10% trimethyl ammonium ethyl acrylate. The results are shown in Table 3.

TABLE 3

| Glyphosate (g/ha) | 0 | 375 | 375 | 375 | 375 |
|---|---|---|---|---|---|
| Polymer | 0 | 0 | Neutral | Anionic | Cationic |
| Regrowth % | 100 | 20.6 | 13.7 | 11.9 | 6.4 |
| Kill | 0 | 79.4 | 86.3 | 88.0 | 93.6 |

Tables 1 to 3 show the improved performance of glyphosate in the presence of polymer.

EXAMPLE 5

The process of Example 2 was repeated in a different series of tests in which assessment was made after 13 days. In one test the same polymer was used as in Example 2. In another test a polymer was used which had similar molecular weight but was polyacrylic acid partially neutralised to pH 5.5. The results are shown in Table 4 from which it is apparent that this polymer that is not made from acrylamide worsens the herbicidal effect.

TABLE 4

| Glyphosate (g/ha) | 0 | 375 | 375 | 375 |
|---|---|---|---|---|
| Polymer | — | — | Polyacrylamide | Polyacrylic acid |
| Regrowth (%) | 100 | 25.7 | 19.0 | 66.2 |
| Kill (%) | 0 | 74.3 | 81.0 | 33.8 |

EXAMPLE 6

A concentrate of 70% Chlormequat chloride was diluted with water and sprayed at 250 l/ha to give 1208 and 1610 g/ha of Chlormequat chloride, with and without 0.1% polymer in the solution. The solutions were sprayed in a replicated field trial on to winter wheat variety Beaver (known to give good response to Chlormequat) at growth stage 31 following standard agricultural practice and immediately prior to harvest samples of wheat were taken from test plots and the straw length measured. The same process was also applied to winter wheat variety Riband (known to give poor response to Chlormequat) and to winter barley variety Marinka. The results are shown in Table 5.

TABLE 5

| Chlormequat g/ha | 0 | 1208 | | 1610 | |
|---|---|---|---|---|---|
| Polymer % | 0 | 0 | 0.1 | 0 | 0.1 |
| Straw Length (cm) | | | | | |
| Beaker | 85.3 | 73.3 | 69.6 | 71.6 | 70.7 |
| Riband | 80.3 | 76.4 | 75.8 | 76.6 | 75.7 |
| Mariuka | 103.1 | 94.3 | 90.0 | 96.3 | 91.1 |

EXAMPLE 7

34 parts of a 12.5% aqueous solution of substantially non-ionic polyacrylamide having IV 2 dl/g was mixed with 66 parts of a 70% by weight aqueous solution of Chlormequat chloride to give an aqueous concentrate containing 46% Chlormequat chloride and 4.3% polymer. This solution was physically and chemically stable.

EXAMPLE 8

The concentrate of Example 7 was diluted in 250 l water to produce a sprayable composition that was sprayed at 1070 and 1610 g/ha Chlormequat in a replicated field trial on to winter barley variety Magi at growth stage 30 (as in Example 6) and it was also sprayed at 1610 g/ha on to linseed, with the straw length or crop height being recorded just prior to harvest. The results are shown in Table 6.

TABLE 6

| Chlormequat g/ha | 0 | | 1070 | | 1610 | |
|---|---|---|---|---|---|---|
| Polymer | 0 | 0 | Ex 5 | 0 | Ex 5 | |
| Wheat Straw Length (cm) | 102.2 | 98.9 | 97.6 | 100.8 | 95.8 | |
| Linseed height (cm) | 54 | | | | 53.7 | 50.4 |

The benefit of providing the Chlormequat with polymer as in Example 7, compared to the application of Chlormequat alone, is clearly shown.

EXAMPLE 9

A commercial formulation of the herbicide and potato dessicant Diquat was diluted to give a sprayable solution containing 400 g/ha, with and without 0.1% non-ionic polyacrylamide intrinsic viscosity 2 dl/g. The solution was sprayed in a replicated field trial on to Pentland Dell potato crop three weeks prior to harvest and the level of dessication was assessed at various times after spraying on a scale 0 to 9 where 0 represents the crop being completely dead and 9 represents the crop showing no damage or reduction in growth. The results are shown in Table 7.

TABLE 7

| Days after spraying | 7 | 14 | 21 |
|---|---|---|---|
| (Control) | 8.0 | 6.0 | 5.0 |
| Diquat | 7.3 | 4.3 | 1.7 |
| Diquat + 0.1% Polymer | 5.7 | 1.5 | 1.0 |

EXAMPLE 10

The same polymer as in Example 1 was used in a series of tests, the results of which are set out in Tables 8 to 15. In each instance the defined active ingredient was diluted to give the quoted dosage in g/ha with or without the polymer in the specified amount and the level of kill assessed on a scale of 0 to 9, as above. In Table 8 the spray was applied on to pots of *T. maritimum* (May weed) at the 2 to 4 leaf stage. In Table 9 it was applied on to *A. myosuroives* (black grass). In Table 10 it was applied on to *A. fatua* (wild oats). In Table 11 it was applied on to *G. aparine* (cleaver). In Table 12 it was applied on to *E. repens* (common couch). In Table 13 it was applied on to *S. media* (chickweed). In Table 14 it was applied on to *V. arvensis* (field pansy). In Table 15 it was applied on to *V. persica* (speedwell).

TABLE 8

| Days after spraying | 7 | 14 | 21 | 28 |
|---|---|---|---|---|
| Control | 9.0 | 9.0 | 9.0 | 9.0 |
| Clopyralid (50 g) | 5.2 | 4.0 | 4.0 | 3.0 |
| Clopyralid (50 g) + 0.025% + Polymer | 5.0 | 4.0q | 2.3 | 1.5 |
| Clopyralid (25 g) | 5.0 | 4.0 | 4.5 | 3.8 |
| Clopyralid (25 g) + 0.025% + Polymer | 5.0 | 4.0 | 2.8 | 1.8 |

TABLE 9

| Days after spraying | 7 | 14 | 21 | 28 |
|---|---|---|---|---|
| Control | 9.0 | 9.0 | 9.0 | 9.0 |
| Fenoxaprop-ethyl (120 g) | 6.8 | 5.8 | 4.5 | 2.8 |
| Fenoxaprop-ethyl (120 g) + 0.1% Polymer | 6.3 | 5.0 | 3.5 | 2.0 |
| Fenoxaprop-ethyl (60 g) | 7.3 | 5.8 | 4.3 | 3.3 |
| Fenoxaprop-ethyl (60 g) + 0.1% Polymer | 7.0 | 5.7 | 3.8 | 2.8 |

TABLE 10

| Days after spraying | 7 | 14 | 21 | 28 |
|---|---|---|---|---|
| Control | 9.0 | 9.0 | 9.0 | 9.0 |
| Fenoxaprop-ethyl (120 g) | 5.7 | 5.7 | 3.7 | 1.3 |
| Fenoxaprop-ethyl (120 g) + 0.1% Polymer | 5.2 | 5.5 | 3.2 | 1.3 |
| Fenoxaprop-ethyl (60 g) | 6.2 | 6.0 | 4.7 | 3.2 |
| Fenoxaprop-ethyl (60 g) + 0.1% Polymer | 5.3 | 5.3 | 3.5 | 1.8 |

TABLE 11

| Days after spraying | 7 | 14 | 21 | 28 |
|---|---|---|---|---|
| Control | 9.0 | 9.0 | 9.0 | 9.0 |
| Mecoprop-P (600 g) | 6.0 | 3.5 | 3.7 | 2.0 |
| Mecoprop-P (600 g) + 0.1% Polymer | 6.0 | 3.3 | 2.2 | 0.8 |
| Mecoprop-P (300 g) | 6.0 | 3.5 | 3.5 | 2.0 |
| Mecoprop-P (300 g) + 0.1% Polymer | 6.0 | 3.3 | 2.2 | 1.2 |

TABLE 12

| Days after spraying | 7 | 14 | 21 | 28 |
|---|---|---|---|---|
| Control | 9.0 | 9.0 | 9.0 | 9.0 |
| Quizalofop-ethyl (125 g) | 8.0 | 4.8 | 3.8 | 2.3 |
| Quizalofop-ethyl (125 g) + 0.1% Polymer | 7.3 | 4.2 | 2.5 | 0.7 |
| Quizalofop-ethyl (62.5 g) | 8.0 | 4.8 | 3.7 | 0.8 |
| Quizalofop-ethyl (62.5 g) + 0.1% Polymer | 7.7 | 3.8 | 1.8 | 0.0 |

TABLE 13

| Days after spraying | 7 | 14 | 21 | 28 |
|---|---|---|---|---|
| Control | 9.0 | 9.0 | 9.0 | 9.0 |
| Fluroxypyr (110 g) | 4.8 | 2.5 | 1.0 | 0.0 |
| Fluroxypyr (100 g) + 0.025% Polymer | 5.0 | 2.3 | 1.2 | 0.0 |
| Fluroxypyr (50 g) | 5.0 | 3.2 | 2.0 | 0.3 |
| Fluroxypyr (50 g) + 0.025% Polymer | 4.8 | 3.0 | 1.0 | 0.3 |
| Fluroxypyr (25 g) | 5.0 | 4.3 | 2.0 | 0.2 |
| Fluroxypyr (25 g) + 0.025% Polymer | 5.0 | 3.7 | 1.5 | 0.0 |

TABLE 14

| Days after spraying | 7 | 14 | 21 | 28 |
|---|---|---|---|---|
| Control | 9.0 | 9.0 | 9.0 | 9.0 |
| Metsulfuron-methyl (3 g) | 7.0 | 5.5 | 4.5 | 3.3 |
| Metsulfuron-methyl (3 g) + 0.1% Polymer | 7.0 | 4.8 | 3.7 | 2.3 |
| Metsulfuron-methyl (1.5 g) | 7.0 | 5.3 | 5.0 | 3.5 |
| Metsulfuron-methyl (1.5 g) + 0.1% Polymer | 7.0 | 5.2 | 4.3 | 2.8 |

TABLE 15

| Days after spraying | 7 | 14 | 21 | 28 |
|---|---|---|---|---|
| Control | 9.0 | 9.0 | 9.0 | 9.0 |
| Metsulfuron-methyl (3 g) | 7.5 | 2.8 | 2.7 | 0.8 |
| Metsulfuron-methyl (3 g) + 0.1% Polymer | 7.3 | 2.5 | 2.2 | 0.5 |
| Metsulfuron-methyl (1.5 g) | 7.5 | 3.2 | 2.8 | 1.0 |
| Metsulfuron-methyl (1.5 g) + 0.1% Polymer | 7.2 | 3.0 | 2.3 | 0.5 |

EXAMPLE 11

A commercial formulation of the herbicide Isoproturon was diluted to give sprayable solutions containing various amounts of Isoproturon, with and without the same polymer as in Example 1.

The solutions were sprayed in a replicated field trial on to a commercial Winter Wheat crop (variety Riband) infester with *A. myosurides* (Blackgrass) in autumn following standard agricultural practice. No phytotoxicity to the wheat was observed with any treatment. The level of kill of Blackgrass was assessed visually.

The results are shown in Table 16.

TABLE 16

| Isoproturon g/ha | 0 | 1250 | 1250 | 1875 | 2500 |
|---|---|---|---|---|---|
| Polymer | 0 | 0 | 0.1 | 0.1 | 0 |
| Blackgrass kill (%) | 0 | 88 | 90.5 | 95.0 | 95.0 |

Thus, at the lowest rate the polymer improves the performance of Isoproturon. A rate of 1875 g/ha Isoproturon with polymer produces a kill achieved with 2500 g/ha in the absence of polymer.

EXAMPLE 12

This examples demonstrates the effect of different polymers on spray angle. Aqueous solutions were prepared containing known weights of (1) a non-ionic polyacrylamide having intrinsic viscosity 2 dl/g, supplied as a 12.5% aqueous solution and (2) a non-ionic polyacrylamide having intrinsic viscosity 8 dl/g, supplied as a 50% inverse phase dispersion (typical of an anti-drift agent).

The solutions were sprayed through a Lurmark Flat Fan 04 80° Nozzle at a pressure of 3 bar, using an Azo Plot Sprayer. The nozzle was held at a known height over a bed of water-absorbent material. From the height of the nozzle and the length of the visible impression on the absorbent material, the spray angle could be calculated.

The results are shown in Table 17.

TABLE 17

| Polymer Concentration (%) | Spray Angle (Degrees) | |
|---|---|---|
| | Polymer IV2 | Polymer IV8 |
| 0 | 87.3 | 87.3 |
| 0.01 | 84.1 | 80.5 |
| 0.025 | 85.1 | 69.0 |
| 0.05 | 83.8 | 71.9 |
| 0.1 | 84.9 | 66.0 |
| 0.25 | 79.9 | — |
| 0.50 | 71.9 | |

Thus the lower M.W. polymer causes substantially no distortion of the spray angle, especially at the concentrations that are preferred for use in the invention.

I claim:

1. An aqueous concentrate comprising an aqueous solution of (a) a water soluble foliar systemic active ingredient and (b) 5 to 25% by weight of a water soluble polymer which is formed of 51 to 100% acrylamide and 0 to 49% ethylenically unsaturated monomer selected from anionic and cationic monomers and has intrinsic viscosity below 3 dl/g.

2. A concentrate according to claim 1 in which the active ingredient is selected from glyphosate, chlormequat, diquat, clopyralid and hormone weedkillers.

3. A concentrate according to claim 1 in which the polymer is formed from 80 to 100% acrylamide and 0 to 20% ethylenically unsaturated anionic monomer.

4. A concentrate according to claim 1 in which the polymer is substantially non-ionic polyacrylamide.

5. An aqueous concentrate comprising an aqueous solution of (a) a water soluble foliar systemic active ingredient and (b) 5 to 25% by weight of a water soluble polymer which is formed of 51 to 100% acrylamide and 0 to 49% ethylenically unsaturated monomer selected from anionic and cationic monomers wherein the amount and molecular weight of the polymer is such that when the concentrate is diluted to provide a sprayable foliar composition the polymer does not substantially affect the spray pattern of the composition.

6. A concentrate according to claim 5 in which the active ingredient is selected from glyphosate, chlormequat, diquat, clopyralid and hormone weedkillers.

7. A concentrate according to claim 5 in which the polymer is formed from 80 to 100% acrylamide and 0 to 20% ethylenically unsaturated anionic monomer.

8. A concentrate according to claim 5 in which the polymer is substantially non-ionic polyacrylamide.

9. An aqueous sprayable foliar composition comprising an aqueous solution or dispersion of a foliar systemic active ingredient in an aqueous solution of 0.005 to 0.5% by weight of the composition of a water soluble polyer of 51 to 100% acrylamide and 0 to 49% ethylenically unsaturated monomer selected from anionic and cationic monomers having a molecular weight such that its presence in the sprayable foliar composition does not substantially affect the spray pattern of the composition.

10. A concentrate according to claim 9 in which the active ingredient is selected from glyphosate, chlormequat, diquat, clopyralid and hormone weedkillers.

11. A concentrate according to claim 9 in which the polymer is formed from 80 to 100% acrylamide and 0 to 20% ethylenically unsaturated anionic monomer.

12. A concentrate according to claim 9 in which the polymer is substantially non-ionic polyacrylamide.

* * * * *